United States Patent [19]
Flowers et al.

[11] Patent Number: 5,571,535
[45] Date of Patent: Nov. 5, 1996

[54] TREATMENT OF TOPICAL INFECTIONS

[76] Inventors: Marianne Flowers; Basilio Tavares, both of 4372 37th St., San Diego, Calif. 92105-1003

[21] Appl. No.: 620,145

[22] Filed: Nov. 30, 1990

Related U.S. Application Data

[63] Continuation-in-part of Ser. No. 389,689, Aug. 3, 1989, abandoned.

[51] Int. Cl.$^6$ ............................... A61K 9/06; A61K 9/10
[52] U.S. Cl. ...................... 424/489; 424/401; 424/78.07; 424/715; 424/722; 424/195.1; 514/937; 514/887
[58] Field of Search ..................................... 424/489, 401, 424/78.07, 715, 722, 195.1; 514/937, 887

[56] References Cited

U.S. PATENT DOCUMENTS 4,369,180   1/1983   Mihalovits ........................... 426/195.1

OTHER PUBLICATIONS

Gennaro. (1985). Remington's Pharmaceutical Sciences, Mack Pub., p. 811.
Berkow et al., The Merck Manual, 15 Edition pp. 2267–2270 & 2327–2328 (1987).
Budavari et al. (1989). The Merck Index, Merck and Co., Inc.

*Primary Examiner*—Raj Bawa
*Attorney, Agent, or Firm*—Knobbe, Martens, Olson & Bear

[57] ABSTRACT

A composition and method for use in treating topical Herpes Simplex 1 infections of the skin, in which the composition comprises a mixture of at least 0.5% by weight of the following ingredients: an alkali metal carbonate; an alkali metal phosphate; and an alkali metal hypochlorite, in a pharmaceutically acceptable topical carrier in the form of a powder, a cream, or a lotion, and the method comprises applying such compositions to the skin at the site of the infection.

11 Claims, No Drawings

TREATMENT OF TOPICAL INFECTIONS

CROSS REFERENCE TO RELATED APPLICATION

This is a continuation-in-part of U.S. patent application Ser. No. 07/389,689, filed Aug. 3, 1989, now abandoned.

BACKGROUND OF THE INVENTION

The present invention relates to a method and composition for treatment of topical bacterial, vital, and fungal infections. It is particularly useful in treatment of cold sores, fever blisters, and other symptoms of herpes simplex I virus infection, as well as other topical infections such as impetigo and ringworm.

There are many people who suffer occasionally or chronically from herpes simplex I, the common cold sore. Cold sores can appear on the lips, around the rim of the mouth, in nostrils, around the rim of the nostrils, and on the upper lip between the nose and the mouth.

A cold sore usually goes through a cycle. The onset is characterized by stinging, vexing, burning, an itching sensation, and swelling and rubification of the skin tissues in the afflicted area. Next comes the development of blisters and continued swelling. Blisters may break and weep.

Finally the blisters begin to shrink and dry, followed by a scab covering. The scab covering is unsightly, as is the entire cold sore process, and even during the scab phase there are often onsets of burning, stinging, and itching. The course of the infection from onset to disappearance is usually about three weeks.

Needless to say, no one wants a cold sore. For those with high profile professions, such as sales personnel, entertainers, actors, and models, the affliction is more than a mere embarrassment; it can mean loss of work. Makeup can cover the problem only partially.

The present invention addresses this problem by providing a method and composition for treating and eliminating the effects of this viral infection. The composition used is an antiviral and antibacterial material.

SUMMARY OF THE INVENTION

The compositions of the present invention may advantageously comprise a mixture of at least 0.5% by weight of each of the following ingredients: an alkali metal carbonate, preferably sodium carbonate or calcium carbonate; an alkali metal phosphate such as sodium phosphate or calcium phosphate; and an alkali metal hypochlorite such as calcium hypochlorite. The balance up to 100% of the composition can be made up of pharmaceutically acceptable diluents, carriers, and excipients, such as corn starch, aloe vera lotion, silica, polysorbates, glycerine, alcohol, water, and the like. The composition may be in the form of a dry powder, a lotion, cream, paste, or ointment. In a preferred embodiment, the alkali metal carbonate comprises a mixture of calcium carbonate and sodium carbonate, most preferably in approximately equimolar amounts.

The method of the present invention requires applying the composition described herein to the site of a topical infection of the skin or mucous membranes, such as the site of a cold sore, impetigo, herpes eruption, ringworm, and the like. The composition is preferably applied as a paste or other spreadable composition having sufficient viscosity to remain localized on the affected area. The liquid vehicle used with the active ingredients is preferably volatile, so that it can evaporate and leave a dry composition on the skin. This dry composition is believed to exert a drawing effect on the affected area, with therapeutic results.

DETAILED DESCRIPTION OF THE INVENTION

The present invention includes a blending of ingredients; active, inactive, cleaning agents and carrier; where said ingredients can provide a treatment or cure for those suffering from symptoms of herpes simplex I, other topical herpes or viral infections, common cold sores and fever blisters, ringworm, impetigo, and other viral, fungal, and bacterial infections of the skin.

The compositions of the present invention may advantageously comprise a mixture of at least 0.5% by weight of each of the following ingredients: an alkali. metal carbonate, preferably sodium carbonate or calcium carbonate; an alkali metal phosphate such as sodium phosphate or calcium phosphate; and an alkali metal hypochlorite such as calcium hypochlorite. The balance up to 100% of the composition can be made up of pharmaceutically acceptable diluents, carriers, and excipients, such as corn starch, aloe vera lotion, silica, polysorbates, glycerine, alcohol, water, and the like. The composition may be in the form of a dry powder, a lotion, cream, paste, or ointment. In a preferred embodiment, the alkali metal carbonate comprises a mixture of calcium carbonate and sodium carbonate, most preferably in approximately equimolar amounts.

In one embodiment. of the invention, the active ingredients of the composition are present in the following weight ratios:

Calcium carbonate 5–10 parts

Sodium carbonate 5–10 parts

Sodium phosphate (anhydrous) 5–10 parts

Calcium hypochlorite 6–12 parts

In another embodiment of the invention, the active ingredients are present in. the following weight ratios:

Calcium carbonate about 7 parts

Sodium carbonate about 7 parts

Sodium phosphate (anhydrous) about 7 parts

Calcium hypochlorite about 8 parts

In still another embodiment, the composition is a wettable powder with the following composition of active ingredients:

Calcium carbonate ($CACO_3$)1.4%

Sodium carbonate ($Na_2CO_3$)1.4%

Sodium phosphate ($Na_2HPO_4$)1.4% (anhydrous)

Calcium hypochlorite (Chlorinol)8%

The remainder of this particular formulation may be a dry, wettable excipient, such as corn starch, modified food starch, fumed silica, and the like.

In any of the compositions, the formulation can also comprise inert ingredients such as corn starch, for blending consistency and control of dosage strength, and blending ingredients, such as aloe lotion, for texture, color, and aroma, in such proportions as desired.

In the practice of the present invention, the dry formulation described above in the Summary of the Invention is combined with water and is applied to the site of the of the infection as a paste. The formulation acts as a cleaning drawing agent as said paste dries. Most importantly, the combination of ingredients effectively kills or renders harmless any active virus of the herpes simplex strain. When applied to a suspected cold sore patch the compound will first clean the area, second draw the fluids of the weeping lesions or watery blisters into the paste and finally the antiseptic qualities of the compound will kill all viruses and bacteria present.

The result is the cold sore is immediately relieved of the vexing pain, stinging and burning sensations common with cold sores. Not only is the pain and discomfort eliminated quickly, but the cold sore itself and the colony of virus which caused the eruption in the first place is eradicated. The sufferer will have the pain vanquished and the cold sore will not erupt later with the unsightly weeping lesions and later scabs. Cold sores will quickly disappear as soon as the application of the remedy is made and they will not reoccur.

By using the compound of the invention, a user can eliminate the initial discomfort and unsightliness of the usual three week period onset, eruption and final healing of a cold sore.

The purpose of the invention is to provide a home remedy which is simple to use and effective against herpes simplex I, the common cold sore, and the other indications mentioned above. The composition should not be taken internally.

The present invention solves the problem of herpes simplex I, cold sores, quickly and permanently. In one preferred embodiment, the ingredients remain dry and ready for use until water is added to form a light paste. When applied, the chemicals first clean the area, next they begin killing of the virus causing the irritation. As the paste dries, it has a drawing effect. This drawing effect will pull the fluid of the weeping lesion into the paste. The most contagious stage is blunted because the fluid containing the virus is pulled into the paste and killed.

At any stage, the compound will be effective against cold sores. Almost instant relief from the horrendous cold sore is achieved. Repeat or continued applications are not necessary as the virus causing the inflammation is killed, leaving the natural body action to take over and return the affected cells to normal.

Persons who have chronic cold sores will hail the compound of the instant invention as a wonder cure.

Although certain preferred embodiments are described, it will be apparent that various modifications, changes, different excipients, and the like can be readily made without departing from the spirit of the invention. Thus, it is intended that the scope of the present invention be measured by the appended claims and their reasonable equivalents.

What is claimed is:

1. A composition packaged for treatment of topical herpes simplex 1 infections of the skin, comprising a mixture of at least 0.5% by weight of the following ingredients: an alkali metal carbonate; an alkali metal phosphate; and an alkali metal hypochlorite, in a pharmaceutically acceptable topical carrier in the form of a powder, a cream, or a lotion, together with sufficient corn starch to provide blending consistency.

2. A composition packaged for treatment of topical herpes simplex 1 infections of the skin, comprising a mixture of at least 0.5% by weight of the following ingredients: an alkali metal carbonate; an alkali metal phosphate; and an alkali metal hypochlorite, in a pharmaceutically acceptable topical carrier comprising aloe lotion.

3. A method for topical treatment of cold sores caused by Herpes simplex I infections of the skin, comprising applying a composition comprising a mixture of at least 0.5% by weight of each of the following ingredients: an alkali metal carbonate; an alkali metal phosphate; and an alkali metal hypochlorite, in a pharmaceutically acceptable carrier to the site of the infection.

4. The method of claim 3, wherein said infection is herpes simplex I.

5. The method of claim 3, wherein the composition is applied in the form of a drying paste.

6. The method of claim 3, wherein the infection is ringworm.

7. The method of claim 3, wherein the alkali metal carbonate comprises a mixture of calcium carbonate and sodium carbonate.

8. The method of claim 3, wherein the ingredients are present in the following weight ratios:

Calcium carbonate 5–10 parts

Sodium carbonate 5–10 parts

Sodium phosphate (anhydrous) 5–10 parts

Calcium hypochlorite 6–12 parts.

9. The method of claim 3, wherein the ingredients are present in the following weight ratios:

Calcium carbonate about 7 parts

Sodium carbonate about 7 parts

Sodium phosphate (anhydrous) about 7 parts

Calcium hypochlorite about 8 parts.

10. The method of claim 3, wherein said excipient comprises sufficient corn starch to provide blending consistency.

11. The method of claim 3, wherein said excipient comprises aloe lotion.

* * * * *